United States Patent [19]
Sitte et al.

[11] Patent Number: 5,469,712
[45] Date of Patent: Nov. 28, 1995

[54] DEVICE FOR DEHYDRATING AND/OR EMBEDDING SAMPLES

[75] Inventors: Hellmuth Sitte, Seefeld in Tirol, Austria; Klaus Neumann, Bexbach-Saar, Germany; Ludwig Edelmann; Helmut Haessig, both of Homburg-Saar, Germany; Anton Lang, Vienna; Heinrich Kleber, Wien/Strebersdorf, both of Austria

[73] Assignee: Leica AG, Vienna, Austria

[21] Appl. No.: 232,152

[22] PCT Filed: Sep. 6, 1993

[86] PCT No.: PCT/EP93/02408

§ 371 Date: May 31, 1994

§ 102(e) Date: May 31, 1994

[30] Foreign Application Priority Data

Sep. 8, 1992 [AT] Austria ................................. 1787/92

[51] Int. Cl.⁶ .................................................. F25B 19/00
[52] U.S. Cl. .............................................. 62/51.1; 62/55.5
[58] Field of Search ............................... 62/51.1, 55.5

[56] References Cited

U.S. PATENT DOCUMENTS

| | | | |
|---|---|---|---|
| 4,232,453 | 11/1980 | Edelmann | 34/92 |
| 4,306,425 | 12/1981 | Sitte et al. | 62/51.1 |
| 4,723,420 | 2/1988 | Sitte | 62/51.1 |

FOREIGN PATENT DOCUMENTS

| | | |
|---|---|---|
| 2739796 | 3/1979 | Germany. |
| 2944464 | 5/1981 | Germany. |
| 3425744 | 1/1986 | Germany. |
| 3610748 | 10/1987 | Germany. |

OTHER PUBLICATIONS

H. Sitte, Zeiss, MEM 3, 1984, pp. 25–31.
Carlemalm et al., "Practical Methods in Electron Microscopy", Journal of Microscopy, vol. 126, Pt 2, May 1982, pp. 123–143.
L. Edelmann, "Freeze–Drying of Chemically Unfixed Biological Material for Electron Microscopy", Mikroskopie, Vienna, 1979, pp. (35), 31–36.
L. Edelmann, "Freeze–Dried Embedded Specimens for Biological Microanalysis", Scanning Electron Microscopy, IV, 1986, pp. 1337–1356.
E. Carlemann et al., "Low Temperature Embedding", The Science of Biological Specimen Preparation, 1986, pp. 147–154.
H. Sitte et al., "An Instrument for Cryosubstitution And Low Temperature Embedding," *GIT Laboratory Medicine*, vol. 10:199–208, (1987).

Primary Examiner—Christopher Kilner
Attorney, Agent, or Firm—Foley & Lardner

[57] ABSTRACT

Device for dehydrating and/or embedding preferably frozen samples, comprising a Dewar vessel (1) filled with liquid nitrogen (2) and a metallic element (4), anchored to the floor (3), of material of good thermal conductivity, which exhibits at its upper end in the region of attachment of the Dewar neck a cover (5) with a metallic cooling surface (6, 7) which corresponds with the complementarily designed lower contact surfaces of the thermostatically heated (9, 10) substitution (PLT) containers (8) or respectively of the lower part of a freeze-drying chamber in a manner which ensures a good heat transfer between the corresponding surfaces.

17 Claims, 2 Drawing Sheets

DEVICE FOR DEHYDRATING AND/OR EMBEDDING SAMPLES

The invention relates to a device for dehydrating and/or embedding samples, especially at temperatures between +20° C. and −120° C., in a sample container at a thermostatically regulated temperature in a Dewar vessel containing liquid nitrogen.

For rapid "immobilization", samples for microscope or electron-microscope investigations are frequently frozen extremely rapidly. Subsequently, the ice contained in the samples is to a large extent removed at temperatures between −80° C. and −120° C. either by polar solvent (eg. methanol: "Cryosubstitution", in this connection cf. inter alia patents DE 29 44 484 C2 or DE 29 44 464 or respectively H. Sitte, ZEISS MEM 3, 25–31, 1984 or H. Sitte et al, GIT Laboratory Medicine, 10, 199–208, 1987, further literature therein) or under vacuum or respectively by reduction of the water vapor partial pressure ("Freeze-drying": in this connection, cf. inter alia patent: DE 27 39 796 or respectively L. Edelmann, Microscopy Vienna, 35, 31–36, 1979, as well as L. Edelmann, Scanning Electron Microscopy, IV, 1337–1356, 1986, further literature therein), so that subsequently the dried samples can be embedded in paraffin or in a suitable plastic material for a subsequent section preparation. An alternative to this process is offered by the "PLT method" (PLT stands for "Progressive Lowering of Temperature; in this connection, cf. inter alia E. Carlemalm et al, J. Microscopy, Oxford 126, 123–143, 1982; further literature references therein), in which the samples are in the first instance chemically fixed, for example in an aldehyde solution, and subsequently cooled during their dehydration in polar media (eg. acetone or methanol) in each instance to that extent to which the freezing point of the mixture falls. The embedding in this case also takes place by UV polymerization of a monomer formulation at temperatures between −30° and −70° C. Both for cryosubstitution and for the PLT method, and also for the freeze-drying, systems have been developed in which in order to reach the required low temperatures and in order to generate a cryosorption vacuum, use is made of liquid nitrogen (hereinafter referred to as LN2). In these systems (cf. cited literature) in accordance with the prior art the containers provided to dry the samples are disposed either in the neck of a Dewar vessel or in its downwardly extended interior; in this case, the LN2 cooling takes place in the Dewar neck indirectly by the progressively formed gaseous nitrogen (hereinafter referred to as GN2) or by removal of heat via interposed solid bodies or in the interior of the Dewar vessel by direct contact with LN2.

A major disadvantage of such systems resides in that each one of these costly arrangements, which must have not only the Dewar vessel to receive the LN2 but also at least one of the control loops for the thermostatic control of the sample temperature as well as monitoring systems to display the LN2 filling level and warning systems to display an excessively low LN2 filling level, is suitable only for one of these low-temperature methods for drying frozen objects, which, in addition, must frequently be carried out alternately on a comparative basis. Thus, there is frequently a requirement to acquire not only a system for cryosubstitution and/or PLT incubation but also an apparatus, equipped similarly in a costly manner, for freeze-drying, if the intention is to carry out competent comparative investigations in this sector of science.

The object of the present invention is to provide an arrangement which is suitable for a plurality of processes.

According to the invention, this object is achieved in that there is disposed in the Dewar vessel a stationary metal cooling surface which is fixedly connected to the latter and is cooled by liquid nitrogen, and in that the sample container which is releasably insertable into the Dewar vessel, exhibits a contact surface which is complementary to the cooling surface and which rests on the stationary cooling surface when the sample container has been inserted, and thus ensures a good heat exchange between the stationary cooling surface and the contact surface which is complementary thereto. For this purpose, the Dewar vessel has a preferably plane and/or cylindrical cooling surface which is in direct or indirect contact with the LN2, the thermal conductivity and material cross-section of the solid-body connection (eg. aluminum of cross-section>10 $cm^2$) causing a thermal resistance which, even in the case of a minimal LN2 filling level in the Dewar vessel, ensures a temperature of the cooling surface which does not substantially differ (<20° C.) from the LN2 boiling point (−196° C.). As mentioned, the stationary cooling surface corresponds, according to the invention, with the complementarily designed contact surfaces of the in each case removable sample container, which is designed as substitution or PLT or freeze-drying container, which surfaces are mutually exchangeable and assure in each instance a good heat exchange, as a result of the complementary design in relation to the stationary cooling surface in the Dewar vessel. It is particularly advantageous if the solid-body connection between the stationary cooling surface in the Dewar vessel and the LN2 in the Dewar interior is a tube and the cooling surface exhibits an opening communicating with this tube.

Having regard to the freezing points of the customary dehydrating or substitution media (−80° C. to −120° C.), it is advantageous to restrict the heat exchange between the stationary cooling surface in the Dewar vessel and the substitution container, which can as a rule also be employed, with appropriate temperature-time control, as PLT container, in that the contact and/or cross-section of the metallic connection between the corresponding surfaces are restricted to those dimensions which just assure a temperature within the desired range, since otherwise the thermostatic heating of this substitution (PLT) container leads to an unnecessarily high LN2 consumption.

Accordingly, it is expedient if the bottom of the thermostatically heated Substitution (PLT) container is covered to a large extent, preferably to the extent of more than 90%, by a preferably plane or disk-shaped thermally insulating layer, which preferably comprises a foamed plastic material, for example styrene foam or polyurethane foam. A further refinement of the substitution (PLT) arrangement can reside in that the container exhibits at its upper side an annular groove and in its center a refilling opening for LN2, which opening corresponds with the refilling opening of the cooling surface disposed to be stationary in the Dewar vessel, so that, in conjunction with a sleeve-shaped design of the contact surface of the container, LN2 can be refilled into the Dewar vessel through a central opening during the customary operation. The device can be refined further in that the Dewar neck can be sealed by a preferably transparent and UV-transmitting cover, which comprises two plates, one of which is secured to a vertically displaceable sleeve and can be lowered into the Dewar neck as far as the upper edge of the substitution (PLT) container, and in which after lifting this displaceable plate, the cover can be moved horizontally to open the substitution chamber. Finally, in order to draw off poisonous vapors (eg. $OSO_4$ additive to the substitution medium or volatile components of the acrylic monomers for low-temperature embedding), which escape together with the vaporizing GN2 from the Dewar neck or substitution space, it is possible to provide an annular draw-off, which conducts these vapors away by means of an exhauster (eg. ventilator) via a pipe into a flue or into the open air.

According to a specific embodiment of the invention, in place of the substitution (PLT) container it is possible to introduce an evacuatable insert for freeze-drying (hereinafter referred to as FD) into the Dewar neck, the preferably plane floor surface of which corresponds in a similar way with the complementary contact surface of the stationary cooling surface in the Dewar vessel and is cooled by this contact to a temperature >−176° C. In the case of a construction using metal of good thermal conductivity, this creates in the interior of the vacuum container large condensation surfaces which, if required, can be increased further by (an) additional condensation surface(s). Similar to the substitution container, this FD chamber also exhibits a thermostatically heated sample tray, which chamber, according to a preferred feature of the invention, is supplied from the same electrical control device.

Further advantages and features of the invention are evident from the description, which follows, of preferred embodiments with reference to the drawings.

FIG. 1 shows a diagrammatic cross-section through a dewar vessel, which exhibits a preferred installation to receive the substitution (PLT) container for an FD chamber and is equipped, by way of example, with a substitution (PLT) container.

Likewise in a diagrammatic cross-section

Figure 1:
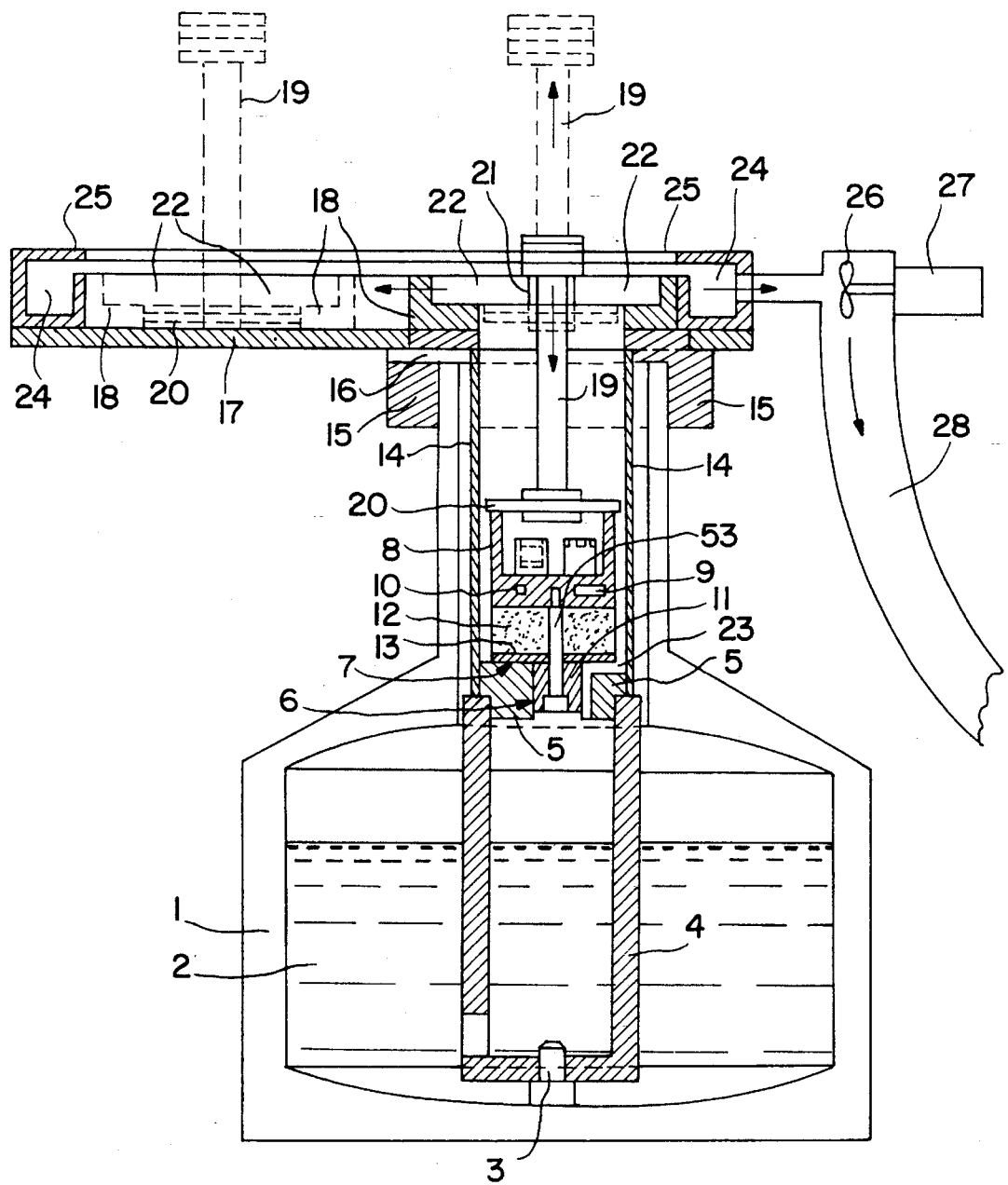

The device according to the invention according to FIG. 1 comprises a Dewar vessel 1 with LN2 filling 2, to the floor element 3 of which a tube 4 of metal of good thermal conductivity (eg. aluminum) is anchored, which tube is sealed off at the top by a cover 5 with a cylindrical recess 6. Tube 4 and cover 5 are situated in a good thermal contact with one another. The cylindrical surface 6 and the plane surface 7 or of the cover form the stationary cooling surfaces, at which the complementary contact surfaces of the substitution chamber 8 [lacuna], which comprises metal of good thermal conductivity and contains a heating cartridge 9 as well as a temperature sensor 10 (eg. Pt100) for the thermostatic control of its temperature. Having regard to the temperature of the container 8 (+20° C. to a minimum of −120° C.), which is required for a cryosubstitution or PLT incubation and/or low-temperature embedding, the metallic thermal contact is restricted to the cross-section of the stay bolt 53 (approximately 1 cm$^2$), which is in good thermal contact with the corresponding cylindrical surface 6 of the cover 5, for example via element 11 and its cylindrical surface 11, and is likewise thermally conductively (screwing) connected to the floor surface of the container 8. The remainder of the floor surface of the container 8 is covered by a thermal insulation 12 (eg. polyurethane foam), the free bottom of which is protected by a sheet metal plate 13. The tube 4 is supported via a cylindrical sleeve 14 of thin-walled fine steel sheet (wall thickness approximately 0.5 mm, height approximately 15 cm) of low thermal conductivity against the annular connection 15, which is secured to the neck of the Dewar vessel and which includes an exit opening 16 for escaping GN2. To the sealing ring 15 there is secured a plate 17, which serves as sliding surface for the cover mounting 18: the displacement takes place in the direction of the arrow to the left after lifting the sleeve 19 with the plate 20 which is secured to it and which for its part seals the substitution or incubation space of the container 8 during the substitution, PLT incubation and/or low-temperature embedding. The sleeve 19 for its part slides in a sleeve 21 which is secured in the cover plate 22. The plates 20 and 22 are preferably constructed from transparent and UV-transmitting material, so that the UV polymerization of acrylic monomers is ensured when the covering is closed. In order to open the "chamber" in the Dewar neck, which chamber is formed by the sleeve 14 in conjunction with the container 8 or respectively the cover 5, the sleeve 19 is lifted vertically in the direction of the arrow with the plate 20 and subsequently the cover 18, 20, 22 is moved horizontally to the left onto the plate 17 (broken-line outlines). Since the "chamber" 5, 8, 14, 15 is constantly flushed with GN2 out of the tube 4 through the recess 23 in the cover 5, gas passes out of the open Dewar neck, which gas frequently includes poisonous components ($OSO_4$ from substitution medium, monomeric acrylic components in the case of low-temperature embedding in acrylic resin) and, according to the invention, is conveyed through a circulating draw-off duct 24 with a slit-shaped opening 25 by means of an exhauster (eg. ventilator 26 on shaft of the motor 27) into the disposal pipe 28.

Figure 2:
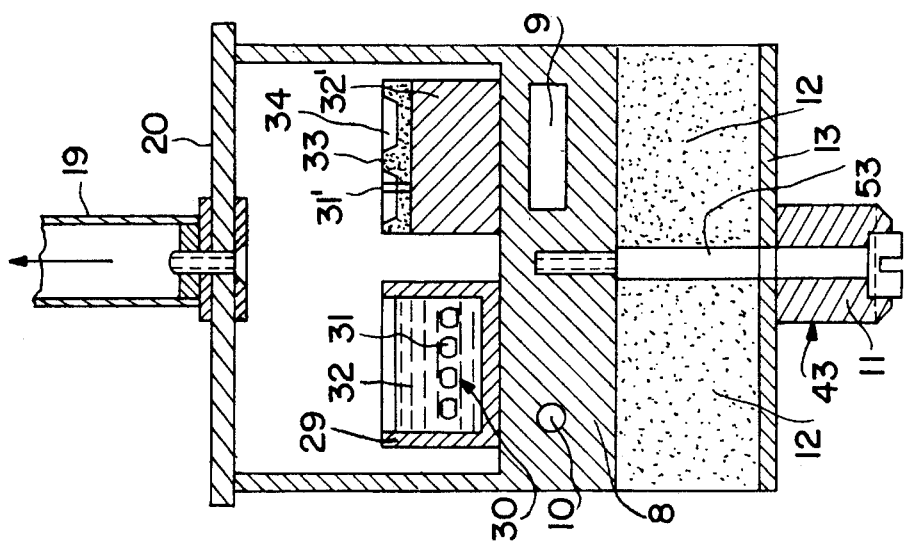
FIG. 2 shows a substitution container similar to FIG. 1, with inserts for substitution or for PLT incubation and flat-embedding of samples.

FIG. 2 shows in detail the substitution container 8 employed in the device according to FIG. 1. On the substitution container 8 the corresponding thermally conductive contact surface is designated by 43. It is further possible to see in the container space a pot 29 with a grid 30 for the laying-on of the frozen samples 31. The pot is filled with the substitution medium 32 (eg. methanol/$OSO_4$). For flat-embedding at low temperature, use is made of an insert 32', 33 the cover plate 33 of which comprises anti-adhesive plastic material (eg. acetal resin) and exhibits hollows to receive the anhydrous samples 31' as well as the synthetic resin monomer 34 (in this connection cf. cited patents and specialist literature). An unreproducible vaporization and escape of individual components from the media 32, 34, is prevented by the sealing with the plate 20 in the already described manner according to the invention.

Figure 3:
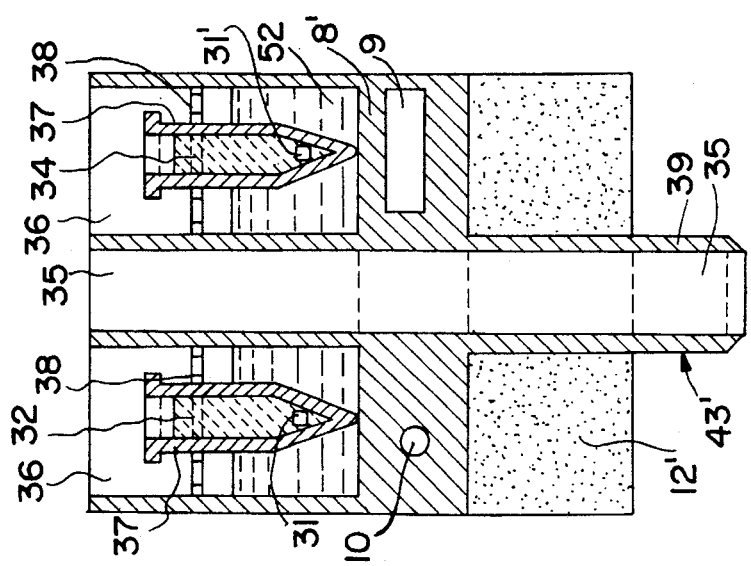
FIG. 3 shows a modified substitution (PLT) container with an annular groove to receive Eppendorf tubes for substitution, PLT incubation and/or low-temperature embedding of samples.

FIG. 3 shows an alternative design of the substitution (PLT) container. The container 8' exhibits a central duct 25 for the refilling of LN2. The reception of the samples 31 takes place in an annular groove 36 of the container 8', for example in Eppendorf tubes 37, which are held in position by a perforated metal sheet 38 and for their part serve to receive the samples 31, 31' as well as the media 32, 34. The thermal contact between the wall of the annular groove 36 and the surfaces of the Eppendorf tubes 37 is in this case ensured in a known manner by a liquid 52 (eg. alcohol). The thermal contact with the cylindrical surface 6 in the cover plate 5 takes place via the sleeve-shaped continuation 39 of the substitution container 8', to be precise via the contact surface 43'.

Figure 4:
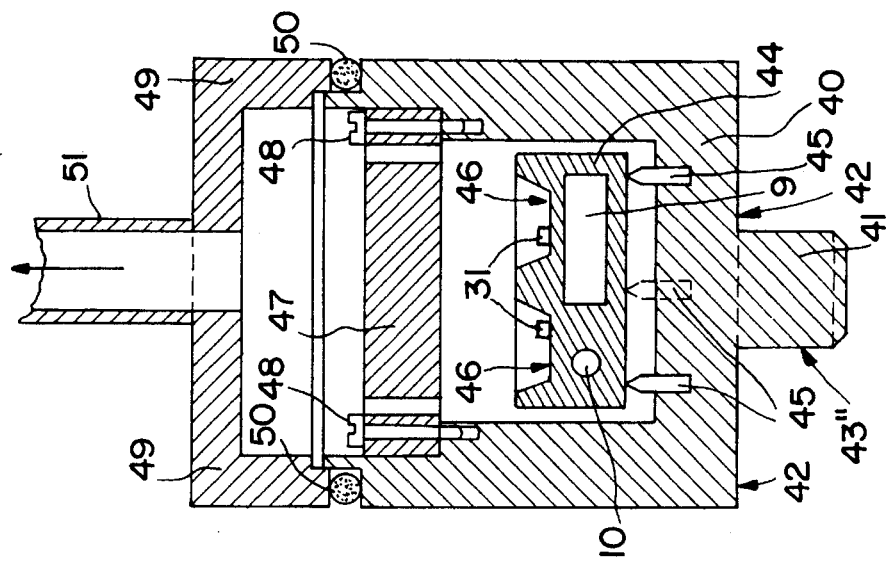
FIG. 4 shows, by way of example, a simple freeze-drying chamber having a pipe connection for evacuation, a sample tray and an additional condensation surface.

FIG. 4 shows an FD chamber, the lower part 40 of which corresponds with the cylindrical continuation 41 via the plane floor surface 42 as well as the cylindrical surface 43" with the complementary surfaces 7 and 6 of the cover 5 on the tube 4 in the Dewar vessel 1 (FIG. 1) and therefore reaches a temperature within the range <−176° C. In the chamber lower part 40 there is situated the sample tray 44 on a mounting (eg. point supports 45) which minimizes the heat transfer 40–44. The sample tray 44 is thermostatically heated by a heating cartridge 9 and a temperature sensor 10 and exhibits at its top hollows 46 to receive the frozen samples 31. The cooling surface can, if required, be increased by the condensation (chrysorption) plate 47, which is secured to the lower part 40 by the screws 48 and is connected thereto with good thermal conductivity. The lower part 40 is connected in a vacuum-tight manner to the upper part 49 of the chamber via a sealing ring 50. The chamber can be evacuated via the draw-off connection 51 at the upper part 49 (arrow).

The arrangement described with reference to FIGS. 1 to 4 can be realized, within the scope of the invention, in various variations and combinations. It is immaterial what inserts are provided in the substitution (PLT) containers 8, 8', 36 or respectively 36 to receive the samples 31, 31' and media 32, 34, as well as in what way the temperature is thermostatically controlled. Further, the realization of the required thermal resistance between the substitution container 8, 8' and the stationary cooling surface 6 or respectively 7 on the cover 5 is immaterial. Likewise, it is immaterial in what way the vacuum for the freeze-drying (eg. rotary pump, diaphragm pump or chrysorption by means of molecular screen) is produced and how the FD chamber is sealed off, so long as in particular the feature of the mutual exchangeability of a substitution PLT container for another or for an FD chamber and vice versa is accomplished in the described and shown manner on account of corresponding complementary heat-exchange surfaces.

We claim:

1. A device for dehydrating and/or embedding samples, comprising:

a sample container and a Dewar vessel, the sample container being removably inserted in the Dewar vessel, and the Dewar vessel containing liquid nitrogen, wherein a stationary metallic cooling surface is disposed within and fixedly connected to the Dewar vessel and is cooled by the liquid nitrogen in the Dewar vessel, and the sample container that is removably inserted in the Dewar vessel has a contact surface that is complementary to the cooling surface and contacts the stationary cooling surface when the sample container is inserted in the Dewar vessel to provide heat exchange between the stationary cooling surface and the contact surface, the device being capable of accepting sample containers for either dewatering or freeze drying a sample and thereafter polymerization embedding of the sample.

2. A device according to claim 1, wherein the sample container is a container for receiving liquid substitution or dehydration media or polymerizable monomers, or is an evacuatable container with a freeze-drying chamber.

3. A device according to claim 1, wherein in the Dewar vessel there is secured a tube of metal of good thermal conductivity, the tube having a cover at the upper end of the tube, the cover being provided with a refilling opening for liquid nitrogen, the upper end of the tube and the cover forming the surfaces for cooling the sample container.

4. A device according to claim 1, wherein the sample container is substantially cylindrical and designed as a substitution (PLT) container, the sample container further comprising a thermostatically heatable vessel, the bottom of which vessel is covered by a plane thermally insulating layer.

5. A device according to claim 4, wherein the thermally insulating layer comprises a foamed plastic material.

6. A device according to claim 4, wherein the bottom of the plane thermally insulating layer is covered with a metal disk.

7. A device according to claim 3, wherein between the sample container and the cover there is situated a cylindrical rod or a cylindrical sleeve, which rod or sleeve exhibits good thermal contact with both the sample container and the cover.

8. A device according to claim 3, wherein the sample container receives other containers containing samples, the sample container having on its upper side an annular groove and in its center a refilling opening for liquid nitrogen, which opening corresponds with the refilling opening in the cover.

9. A device according to claim 1, wherein the neck of the Dewar vessel is sealed by a cover, the cover having a mounting that is horizontally movable and a plate that is vertically movable within the neck of the Dewar vessel.

10. A device according to claim 9, wherein the two plates comprise a transparent material that is UV-transmitting.

11. A device according to claim 1, characterized in that at the upper end of the Dewar neck there is disposed an annular draw-off, which receives the gas escaping from the interior of the Dewar and conducts the gas away by means of an exhauster through a pipe.

12. A device according to claim 1, wherein the sample container is a substantially cylindrical container with a freeze-drying chamber and is insertable into the neck of the Dewar vessel, and wherein the configuration of the bottom of the cylindrical container corresponds with the cover in such a manner that good heat exchange between the two corresponding surfaces is ensured by a complementary design of the surfaces.

13. A device according to claim 12, wherein both the thermostatically heated sample mounting and the condensation surfaces are cooled to the respectively required temperatures exclusively by means of liquid nitrogen via metallic intermediate members.

14. A device according to claim 3, wherein the top of the cover is plane and horizontal.

15. A device according to claim 3, wherein the refilling opening provided on the cover is cylindrical.

16. A device according to claim 5, wherein the foamed plastic material is styrene.

17. A device according to claim 5, wherein the foamed plastic material is polyurethane foam.

\* \* \* \* \*